United States Patent [19]

Kroll

[11] Patent Number: 5,342,399
[45] Date of Patent: Aug. 30, 1994

[54] IMPLANTABLE DEFIBRILLATOR SYSTEM HAVING A SMALL CAPACITANCE VALVE

[75] Inventor: Mark W. Kroll, Minnetonka, Minn.

[73] Assignee: Angeion Corporation, Plymouth, Minn.

[21] Appl. No.: 808,722

[22] Filed: Dec. 17, 1991

[51] Int. Cl.$^5$ .................................. A61N 1/39
[52] U.S. Cl. ........................................ 607/5
[58] Field of Search ........................... 128/419

[56] References Cited

U.S. PATENT DOCUMENTS

| | | | |
|---|---|---|---|
| 3,236,239 | 2/1966 | Berkovits | 128/419 D |
| 3,389,704 | 6/1968 | Buchowski et al. | 128/419 D |
| 4,168,711 | 9/1979 | Cannon, III et al. | 128/419 D |
| 4,708,145 | 11/1987 | Tacker et al. | 128/419 PG |
| 4,821,723 | 4/1989 | Baker, Jr. et al. | 128/419 D |
| 5,131,388 | 7/1992 | Pless et al. | 128/419 D |

OTHER PUBLICATIONS

Peleska, B., "Optimal Parameters of Electrical Impulses for Defibrillation by Condenser Discharges", Cir. Research, vol. XVIII, pp. 10–17, Jan. 1966.
Schuder, J., Stoeckle, H., Gold, J., Keskar, P., "Experimental Ventricular Defibrillation with an Automatic and Completely Implanted System", Trans. Am. Soc. Artif. Organs, vol. 15, pp. 207–212, 1970.
R. A. Winkle, R. H. Mead, M. A. Ruder, et al., "Long-term outcome with the implantable cardioverter-defibrillator," *J. Am Coll Cardiol.*, vol. 13, pp. 1353–1361, 1989.
M. H. Lehman, S. Saksena, "Implantable cardioverter-defibrillators in cardiovascular practice: Report of the policy conference of the North American Society of Pacing and Electrophysiology," *PACE*, vol. 14, pp. 969–979, Jun. 1991.
R. A. Winkle, "State-of-the-Art of the AICD," *PACE*, vol. 14, pp. 961–966, May 1991 pt. ii.
N. G. Tullo, S. Saksena, R. B. Krol, "Technological improvements in future implantable defrillators," *CARDIO*, vol. 7, pp. 107–111, May 1990.
D. P. Zipes, J. Fischer, R. M. King, et al., "Termination of ventricular fibrillation in dogs by depolarizing a critical amount of myocardium," *Am J Cardiol.*, vol. 36, pp. 37–44, Jul. 1975.
P. S. Chen, N. Shibata, E. G. Dixon, et al., "Comparison of the defibrillation threshold and the upper limit of ventricular vulnerability," *Circulation*, vol. 73 #5, pp. 102–1028, May 1986.
A. C. Guyton and J. Satterfield, "Factors concerned in defibrillation of the heart, particularly through the unopened chest," *Am J of Physiology*, vol. 167, p. 81, 1951.
J. C. Schuder, G. A. Rahmoeller, and H. Stoeckle, "Transthoracic ventricular defibrillation with triangular and trapezoidal waveforms," *Circ. Res.*, vol. 19, pp. 689–694, Oct. 1966.
W. A. Tacker, L. A. Geddes, J. McFarlane, et al., "Optimum current duration for capacitor-discharge defibrillation of canine ventricles," *J. Applied Physiology*, vol. 27 #4, pp. 480–483, Oct. 1969.
R. S. MacKay and S. E. Leeds, "Physiological effects of condenser discharges with application to tissue stimulation and ventricular defibrillation," *J. Applies Physiology*, vol. 6, pp. 67–75, Jul. 1953.
W. B. Kouwenhoven and W. R. Milnor, "Treatment of (List continued on next page.)

*Primary Examiner*—William E. Kamm
*Assistant Examiner*—Kennedy J. Schaetzle
*Attorney, Agent, or Firm*—Patterson & Keough

[57] ABSTRACT

The present invention uses the chronaxie, a characteristic time that enters into heart defibrillation. The present invention defines a figure of merit for physiologically effective current for characterizing and evaluating a defibrillation pulse. Using this figure of merit then, the present invention compares defibrillation-pulse options to determine optima for capacitance, tilt and pulse duration. The combined abilities of optima determination and quantitative comparison of options provides for shorter pulses and lower capacitance values than have been in common use in the prior art. The overall result of the present invention is the specifying of smaller, more efficient implantable defibrillator capacitor design.

8 Claims, 2 Drawing Sheets

OTHER PUBLICATIONS ventricular fibrillation using a capacitor discharge," *J. Applies Physiology*, vol. 7, pp. 253–257, Nov. 1957.

R. C. Balagot, W. S. Druz, M. Ramadan, et al., "A monopulse DC current defibrillator for ventricular defibrillation," *J. Thoracic and Cardiovasc. Surgery*, vol. 47 #4, pp. 487–504, Apr. 1964.

J. C. Schuder, H. Stoeckle, J. A. Wes, et al., "Transthoracic ventricular defibrillation in the dog with truncated and untruncated exponential stimuli," *IEEE Trans. Biom. Eng.*, vol. BME-18 #6, pp. 410–415, Nov. 1971.

J. D. Bourland, W. A. Tacker, and L. A. Geddes, "Strength duration curves for trapezoidal waveforms of various tilts for transchest defibrillation in animals," *Med. Instr.*, vol. 12 #1, pp. 38–41, 1978.

J. D. Bourland, W. A. Tacker, L. A. Geddes, et al., "Comparative efficacy of damped sine wave and square wave current for transchest ventricular defibrillation in animals," *Medical Instrum.*, vol. 12 #1, pp. 38–41, 1978.

L. A. Geddes, M. J. Niebauer, C. F. Babbs, et al., "Fundamental criteria underlying the efficacy and safety of defibrillating current waveforms," *Med. Biol. Eng. Comp.* vol. 23, pp. 122–130, 1985.

M. S. Chang, H. Inoue, M. J. Kallok, et al., "Double and triple sequential shocks reduce ventricular defibrillation threshold in dogs with and without myocardial infarction," *J. Am. Coll. Cardiol.*, vol. 8 #6, pp. 1393–1405, Dec. 1986.

D. L. Jones, G. J. Klein, G. M. Guiraudon, "Internal cardiac defibrillation in man: pronounced improvement with sequential pulse delivery to two different orientations," *Circulation*, vol. 73 #3, pp. 484–491, Mar. 1986.

C. F. Babbs and S. J. Whistler, "Evaluation of the operating internal resistance, inductance, and capacitance of intact damped sine wave defibrillators," *Medical Instrum.*, vol. 12 #1, pp. 34–37, Jan.-Feb. 1978.

L. A. Geddes and W. A. Tacker, "Engineering and physiological considerations of direct capacitor-discharge ventricular defibrillation," *Med. and Biol. Eng.*, vol. 9, pp. 185–199, 1971.

P. A. Rubio and E. M. Farrell, "Low-Energy direct defibrillation of the human heart," vol. pp. 32–33, 1978.

C. F. Dahl, G. A. Ewy, E. D. Warner, et al., "Myocardial necrosis from direct current counter-shock: effect of paddle electrode size and time interval between discharges," *Circulation*, vol. 50, p. 956, 1974.

J. A. Pearce, J. D. Bourland, W. Neilsen, et al., "Myocardial stimulation with ultrashort duration current pulses," *PACE*, vol. 5, pp. 52–58, Jan.-Feb. 1982.

IMPLANTABLE DEFIBRILLATOR SYSTEM HAVING A SMALL CAPACITANCE VALVE

BACKGROUND OF THE INVENTION

1. Field of the Invention

The present invention relates generally to defibrillation processes, and more particularly, to a realization that there exists an optimum capacitor values for defibrillation-pulse generation in an implantable system, capacitor values smaller than is now recognized heretofore.

2. Description of the Prior Art

Defibrillation, or causing the cessation of chaotic and uncoordinated contraction of the ventricular myocardium by application of an electrical voltage and current, in its most primitive form goes back to the last century. (J. L. Prevost and F. Batelli, "Sur Quelques Effets des Descharges Electriques sur le Couer des Mammifers", Comptes Rendus Hebdomadaires des Seances de L'Acadmie des Sciences, Vol. 129, p. 1267, 1899.) The sophistication and effectiveness of defibrillation techniques has grown rapidly in subsequent decades. One of the most recent developments has been the practical advent of implantable defibrillation systems. (R. A. Winkle, et al., "Long-term Outcome with the Implantable Cardioverter-Defibrillator", J. Am. Coll. Cardiol., Vol. 13, p. 1353, 1989; M. H. Lehman and S. Saksena, "Implantable Cardioverter-Defibrillators in Cardiovascular Practice: Report of the Policy Conference of the North American Society of Pacing and Electrophysiology", PACE Vol. 14 p. 107 May, 1990.) With the acceptance of this technology, the new challenge is to reduce system size while preserving its effectiveness, in order to improve the patient's quality of life and to extend the range of application of such systems. (R. A. Winkle, "State of the Art of the AICD", PACE Vol. 14, p. 961, May, 1991, part II; N. G. Tullo, S. Saksena, and R. B. Krol, "Technological Improvements in Future Implantable Defibrillators", CARDIO, Vol. 7, p. 107, May, 1990.) Until an ability to anticipate fibrillation has been achieved, it will be necessary to achieve defibrillation by passing a large current through the heart. The current must be large enough to depolarize a large fraction of the myocardium, thus extinguishing depolarization wavefronts. (D. P. Zipes, et al., "Termination of Ventricular Fibrillation in Dogs by Depolarizing a Critical Amount of Myocardium", Am. J. Cardiol , Vol. 36, p. 37, July, 1975.) Further, the waves must be strong enough so that the cells will not be stimulated during their vulnerable periods, causing refibrillation. (P. S. Chen, et al., "Comparison of the Defibrillation Threshold and the Upper Limit of Ventricular Vulnerability", Circulation, Vol. 73, p. 102, May, 1986.)

The high values of current that are employed generally in defibrillation procedures, the compactness that is essential in implantable systems are conflicting requirements. For this reason, a huge premium is placed on knowledge of optimal values for various defibrillation-pulse characteristics; an optimum pulse will avoid the "waste" of current, charge, voltage, or energy, depending on which of these variables prove most relevant to successful defibrillation.

The components that dominate the physical volume of an implantable system are the capacitor and the battery, and here the avoidance of overdesign is crucial. A corollary to the proposition just stated is that accurate knowledge of which of the several defibrillation-pulse variables are dominant has an equally large premium placed upon it when an implantable defibrillator is to be designed. The present invention will address this challenge.

For reasons of simplicity and compactness, capacitor-discharge systems are almost universally used in defibrillation. Achieving the requisite electric field needed to depolarize most of the myocardial cells requires current density above a certain threshold value, and via Ohm's law, this means the process is favored by achieving sufficiently low electrical resistance in the discharge path. For this reason, the use of electrodes of relatively large surface area has for a long time been the norm. (A. C. Guyton and J. Satterfield, "Factors Concerned in Defibrillation of the Heart, Particularly through the Unopened Chest", Am. J. of Physiology, Vol. 167, p. 81, 1951.) The discharge of a capacitor C through a fixed resistance R results in a voltage-versus-time curve (and hence, current versus time as well) that is a declining exponential function, with a characteristic time given by the product RC. But, it has also been recognized for some time that the low-voltage (and low-current) "tail" of the capacitor-discharge pulse is detrimental. (J. C. Schuder, G. A. Rahmoeller, and H. Stoeckle, "Transthoracic Ventricular Defibrillation with Triangular and Trapezoidal Waveforms", Circ. Res., Vol. 19, p. 689, October, 1966; W. A. Tacker, et al., "Optimum Current Duration for Capacitor-Discharge Defibrillation of Canine Ventricles", J. Applied Physiology, Vol. 27, p. 480, October, 1969.) The exact reason for this detrimental effect is not known, although plausible speculations exist.

Efforts to deliver a more nearly rectangular pulse over thirty years ago employed a series inductor in the discharge path, and improved results over the simple RC discharge were noted. (R. S. MacKay and S. E. Leeds, "Physiological Effects of Condenser Discharges with Application to Tissue Stimulation and Ventricular Defibrillation", J. Applied Physiology, Vol. 6 p. 76, July, 1953; W. B. Kouwenhoven and W. R. Milnor, "Treatment of Ventricular Fibrillation Using a Capacitor Discharge," J. Applied Physiology, Vol. 7, p. 253, November, 1957.) Subsequent further efforts in the same direction used RLC (resistor-inductor-capacitor) delay lines, and reported further improvement ((R. C. Balagot, et al., "A Monopulse DC Defibrillator for Ventricular Defibrillation", J. Thoracic and Cardiovascular Surgery, Vol. 47, p. 487, April, 1964.) But fortunately, inductors are bulky components that are unattractive for incorporation in defibrillator systems, especially in implantable systems. For this reason, most efforts have been directed at time-truncated capacitor discharges. (J. C. Schuder, et al. "Transthoracic Ventricular Defibrillation in the Dog with Truncated and Untruncated Exponential Stimuli", IEEE Trans Biom. Eng., Vol. BME-18, p. 410, November, 1971.) That is, the capacitor discharge is simply interrupted by opening a switch at some middle point, typically, approximately at the time that the characteristic "RC time" has been reached. The advent of compact solid-state switches has made such pulse tailoring a straightforward matter. The amount of voltage decline (and current decline, assuming the heart to constitute a linear resistor) that has occurred at the time of pulse termination, is termed the tilt of the pulse. In algebraic language, $$\text{tilt} = (V_{initial} - V_{final})/V_{initial} \qquad \text{Eq. 1}$$

Since the amplitude declines in one characteristic time to 1/e of its initial value, where e is the base of the Napierian system of logarithms, the tilt of a pulse terminated at the RC time is about 0.63, or 63%, to use the customary description. Typical values employed in monophasic defibrillation fall in the range from 60% to 70%.

The many studies that have been published on optimal defibrillation-pulse properties have tended to focus on the energy stored in the capacitor, or charge times voltage. But with the truncation of the pulse, this total energy is unrelated to the energy delivered to the heart unless a number of other variable values are specified. Furthermore, in conventional systems, the residual charge stored in the capacitor is not recovered. Thus, if one's aim, as at present, is to minimize the size and volume of an implantable defibrillation system, total stored energy is not a very useful criterion. Far more relevant is the optimal capacitance. And given a particular value for the heart's resistance, the 50 ohms being a representative value for electrodes of typical design, then the amount of tilt is uniquely related to capacitance for a given pulse duration, and becomes an equally meaningful quantity. Finally, the pulse-duration optimum needs careful study.

After exhaustive scrutiny of published data in the literature, the prior art has not found at this time no determinations of optimal tilt or pulse duration for a capacitor of arbitrary size, nor any attempt to define an optimal value of capacitance for an implantable defibrillator.

The present invention, at this time, has found a rich fund of data on defibrillation-pulse effectiveness that provides a determination of the associated tilts and pulse durations used by those researchers. Furthermore, an extension of well-accepted physiological models results in a model that predicts optimal tilt and pulse duration for an arbitrary capacitance, and also predicts the optimal capacitance for an implantable defibrillator.

SUMMARY OF THE INVENTION

The pioneer physiologist, L. Lapicque, collected substantial amounts of data on the amount of current required for tissue stimulation, using constant-current pulses of various durations. (L. Lapicque, "Definition Experimentelle de l'excitabilite", Proc. Soc. de Biol., Vol. 77, p. 280, 1909.) He established an empirical relationship between the current I and the pulse duration $d_p$, having the form:

$$I = K_1 + (K_2/d_p) \qquad \text{Eq. 2}$$

Thus, the necessary current and the pulse duration are related by a simple hyperbola, shifted away from the origin by the amount of the constant term $K_1$. Multiplying this expression through by $d_p$ yields an expression in charge, rather than current, and constitutes an earlier and consistent equation given by Weiss. (G. Weiss, "Sur la Possibilite de Rendre Comparable entre Eux les Appareils Suivant a l'Excitation Electrique", Arch. Ital. de Biol., Vol. 35, p. 413, 1901). Thus, the stimulating current required in a pulse of infinite duration is $K_1$, a current value Lapicque termed the rheobase. Shortening the pulse required progressively more current, and the pulse length that required a doubling of current for excitation, or $2K_1$, he termed the chronaxie, $d_c$. Substituting $2K_1$ and $d_c$ into Eq. 2 in place of I and $d_p$, respectively, thus yields:

$$d_c = K_2/K_1 \qquad \text{Eq. 3}$$

Lapicque's model described cell stimulation, rather than defibrillation. Bourland demonstrated that defibrillation thresholds in dogs and ponies followed the Lapicque model, provided average current is used in the exercise. (J. D. Bourland, W. Tacker, and L. A. Geddes, "Strength-Duration Curves for Trapezoidal Waveforms of Various Tilts for Transchest Defibrillation in Animals", Med. Instr., Vol. 12, p. 38, 1978.) In a companion paper, the same workers showed that average current is a useful and consistent measure of defibrillation effectiveness for time-truncated pulses of a given duration through a substantial range of durations, from 2 to 20 milliseconds; in other words, so long as the exponential "tail" is eliminated, pulse effectiveness is not very dependant upon waveform details. (J. D. Bourland, W. Tacker and L. A. Geddes, "Comparative Efficacy of Damped Sine Waves and Square Wave Current for Transchest Defibrillation in Animals", Med. Instr., Vol. 12, p. 38, 1978.) From the observations by Bourland and co-workers, the present invention has inferred a heart chronaxie time of 3.6 ms.

To the data of Bourland, the present invention has added values taken from the work of Wessale, et al. on dogs, and Jones, et al. on chicks, both of which groups gave curves of current value versus pulse duration, and these both yielded chronaxie times of 1.8 milliseconds. Further, it has been possible to calculate chronaxie time from data published by Gold (calf, 2.7 milliseconds), Niebauer (dog, 4.1 milliseconds), Feeser (dog, 2.0 milliseconds), and Geddes (dog, averaged from curves for pulses of different tilts, 2.8 milliseconds). This synopsis yields an average chronaxie time of 2.7 milliseconds, and a median value of 2.7 milliseconds also. All of this work is relatively recent, being clustered in the time period from 1977 to 1990.

Building upon these models and data, the general purpose of the present invention has defined a "sufficiency ratio" the ratio of Bourland's ruling average current and the current needed for defibrillation according to the Lapicque model for a hart of a given $K_1$, rheobase current, and a given $K_2$, a charge. This in turn leads to a "physiologically effective current" or $I_{pe}$, that characterizes a particular defibrillation pulse as illustrated in FIG. 3. That is, $I_{pe}$ is a figure of merit that it to be maximized. The challenge is to do so for a given pulse energy and heart resistance by varying pulse duration.

The analysis shows that the optimum pulse duration is approximately the average of the chronaxie time of the heart, the somewhat shorter RC time defined by interelectrode heart resistance, and the value of the defibrillation capacitor. This is an intuitively reasonable result in light of the above suggesting that the duration of a defibrillation pulse should be "tuned" to a natural characteristic time associated with the heart. While limited work has been reported on defibrillation with shorter pulses than those that have become standard, the advantages have not been realized. (L. A. Geddes, et al., "Fundamental Criteria Underlying the Efficacy and Safety of Defibrillating Current Waveforms", Med. Biol. Eng. Comp., Vol. 23, p. 122, 1985.) Short pulses have, in the past, been employed in the context of pacing. (J. A. Pearce, et al,, "Myocardial Stimulation with Ultrashort Duration Current Pulses", PACE, Vol. 14, p. 716, April, 1991.)

Further analysis in terms of physiologically effective current demonstrates that nonobvious fact that there also exists a capacitance optimum, a value that is independent of energy stored; the stored energy can, of course, be altered by varying voltage, but doing so does not alter the best choice of capacitance. To determine optimal capacitance, one writes an expression for $I_{pe}$ as a function of E, R, C and $d_c$, and differentiates it with respect to C. Energy appears only as a factor, and drops out when the expression is equated to zero to find the extremum of the transcendental expression. The result, numerically determined, is:

$$C = (0.8 d_c)/R \qquad \text{Eq. 4}$$

This expression further emphasizes that the RC product associated with the pulse must approximate the chronaxie time, $d_c$. Assuming the chronaxie time of 2.7 milliseconds as cited before and the typical interelectrode resistance of 50 ohms, one finds an optimal capacitance value of 43 uF.

The fact that the most favorable value of capacitance is much lower than that typically employed, 140 uF, is of course highly significant. It permits a size reduction and optimum performance improvement at the same time. In two cases, others have used capacitance values in the neighborhood of 50 uF, but as an incidental matter while focusing on their primary interest in studying the effectiveness of pulse sequences. The intrinsic benefit of the smaller capacitor went unnoted in both cases. An animal study used 50 uF specifically. (M. S. Chang, et al., "Double and Triple Sequential Shocks Reduce Ventricular Defibrillation Threshold in Dogs With and Without Myocardial Infarction", JACC, Vol. 8 p. 1392.) In a contemporaneous human study, capacitance is not cited, but can be inferred to lie in the range from 40 uF to 50 uF. (D. L. Jones, et al., ∓Internal Cardiac Defibrillation in Man: Pronounced Improvement with Sequential Pulse Delivery in Two Different Lead Orientations", Circulation, Vol. 73, p. 484, March, 1986.)

An extension of the analysis given above provides for determination of optimal tilt. For the numbers cited there (2.7 milliseconds, 50 ohms, and 43 uF), it amounts to about 72%. But, if other factors dictate changes in capacitance value, then optimal tilt also changes. For example, at 100 uF, tilt should be about 58%, and at 250 uF, about 50%.

Knowledge of optimal values makes it possible to effect performance and efficiency improvements. For example, present technology typically employs a 140-uF capacitor charged to 750 V, and an associated energy storage of 39.4 J. Although energy stored is not simply related to the defibrillation effectiveness of a system, it remains a crucial design factor because it is proportional to the physical volume of the capacitor. The physiologically effective current for such a system is $I_{pe} = 6.79$ A. Now return to the capacitor value of 43 uF and tilt of 72%. The same value of $I_{pe}$ could be delivered with a stored energy of only 30.7 J and an initial voltage of 1195V. In other words, the conventional design requires 28% more energy, and hence 28% more volume, to meet the figure of merit achieved in the system of the present invention. It might well require higher battery volume as well, although additional factors can affect that determination.

It must be conceded that voltages near and above 1000 V are troublesome with present-day electronic switches, but compromise is possible. For example, an 85 uF capacitor charged to 878 V, and discharged for a tilt to 61% will provide the same $I_{pe}$ as before, but do so with a stored energy of only 32.8J. In this compromise case, the conventional system requires over 20% more energy storage, and hence 20% more capacitor volume than does the new design.

At the present state of the art, the capacitor technology yielding the highest energy density is that of the double-anode, etched-foil aluminum capacitor. These have a rating of 375 V in pulse applications. Two such capacitors, each of 178 uF, placed in series will provide 85 uF chargeable to 750 V, for an $I_{pe}$ of 5.8A, and a required storage of only 24 J. With the conventional 140 uF capacitor charged to 64 V and discharged to 65% tilt, a total storage of 28.7 J is necessary. Hence once again, the conventional system requires over 20% more energy storage and 20% more capacitor volume than does the new design of the present invention.

In general, the new options in the present invention design involve reducing pulse duration to approach more nearly the heart's chronaxie time, thus increasing effective current, or reducing pulse duration and capacitor value to reduce device size. This is in contrast to the conventional design strategy of boosting capacitor value in order to produce "high-energy-output" systems that may marginally improve defibrillation effectiveness, while at the same time boosting system volume and size as well. Numerous studies have demonstrated that stored energy and pulse energy are at best, insufficient measures of effectiveness. (C. F. Babbs and S. J. Whistler, "Evaluation of the Operating Internal Resistance, Inductance and Capacitance of Intact Damped-Sine-Wave Defibrillators", Medical Instrum., Vol. 12, p. 34, January–February, 1978.) Furthermore, pulses of greater-than-optimal duration are at best wasteful, and at worst, detrimental.

The analytical findings for the present invention are the basis as summarized below:

1. The optimal value of defibrillation capacitance is relatively constant, being a function only of the chronaxie and the interelectrode resistance. It is not determined by any stored-energy or delivered-energy limitation or requirement.

2. The optimal tilt is in turn a function of capacitance, and ranges from 50% to essentially 100%.

3. The optimal pulse duration for a given capacitance value is a compromise between the heart's chronaxie time and the RC time of the system, where R is interelectrode resistance and C is the value of the defibrillation capacitor. Thus, this optimal duration is not a constant.

4. Since chronaxie times are typically in the 2-to-4 millisecond range, and the durations recommended here exceed the chronaxie time, these recommendations fall in a safe range; it has been shown that pulses 2 ms or less in duration either do not defibrillate, or do not restore normal function in a reasonable time. (L. A. Geddes and W. A. Tacker, "Engineering and Physiological Considerations of Direct Capacitor-Discharge Ventricular Defibrillation", Med. Biol. Eng., Vol. 9, p. 185, 1971.)

5. Rather than maximizing energy for effective defibrillation, one should maximize effective current while minimizing the energy required to achieve a given level, this to minimize myocardial damage. (P. A. Rubio and E. M. Farrell, "Low-Energy Direct Defibrillation of the Human Heart", Ann. Thoracic Surgery, Vol. 27(1), p. 32, January, 1978; C. F. Dahl, et al., "Myocardial Necrosis from Direct Current Countershock: Effect of Paddle Electrode Size and Time Interval Between Discharges", Circulation, Vol. 50, p. 956, November, 1974.)

Significant aspects and features of the present invention include the use of a defibrillation capacitor smaller than 100 uF.

Another significant aspect and feature of the present invention is a reduction of capacitor volume and system volume for a given degree of defibrillation effectiveness.

Still another significant aspect and feature of the present invention is an increase in defibrillation effectiveness for a given capacitor volume and system volume.

A further significant aspect and feature of the present invention is the recognition and calculation of an optimal capacitance value.

Other significant aspects and features of the present invention is the recognition and calculation of an optimal tilt and the recognition and calculation of an optimal pulse duration.

Another significant aspect and feature of the present invention is the definition of a figure of merit termed physiologically effective current.

Another significant aspect and feature of the present invention is the use of a relatively short defibrillation pulse.

Another significant aspect and feature of the present invention is minimizing the energy that must be stored to deliver a defibrillation pulse of a given physiologically effective current.

Having thus described the embodiments of the present invention, it is a principal object of the present invention to use a defibrillation capacitor smaller than 100 uF.

One object of the present invention is a reduction of capacitor volume and system volume for a given degree of defibrillation effectiveness.

Another object of the present invention is an increase of defibrillation effectiveness for a given capacitor volume and system volume.

Still another object of the present invention is to achieve defibrillation with less energy than that required in the prior art.

Other objects of the present invention is the determination of an optimal capacitance value, the determination of an optimal tilt, and the determination of an optimal pulse duration.

A still further object of the present invention is the definition of a figure of merit for defibrillation-pulse effectiveness, the physiologically effective current, and the effective use of a relatively short defibrillation pulse.

A further object of the present invention is minimizing the energy that must be stored to deliver a defibrillation pulse of a given effectiveness.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

FIG. i illustrates a strength duration curve of current required versus pulse duration, and as defined by equation 2.

Figure 1:
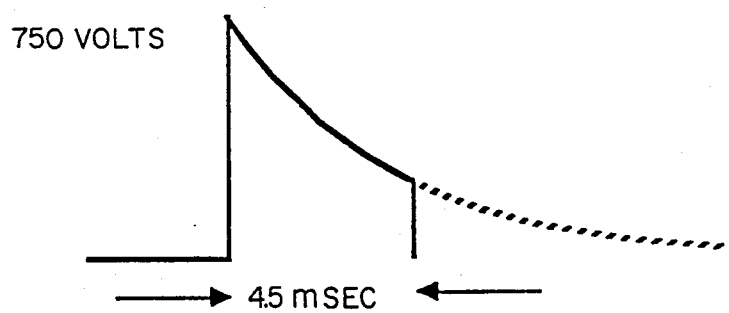
FIG. 1 illustrates a strength duration curve of current required versus pulse duration.
Figure 2:
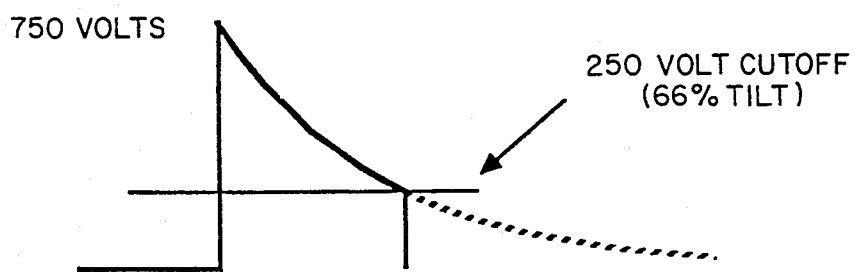
FIG. 2 illustrates a curve of tilt versus capacitance.

FIG. 2 illustrates a curve of tilt versus capacitance and as also defined by the equations below and as also discussed on page 11, lines 17–23. An optimal capacitance range is 20–100 uF.

Figure 3:
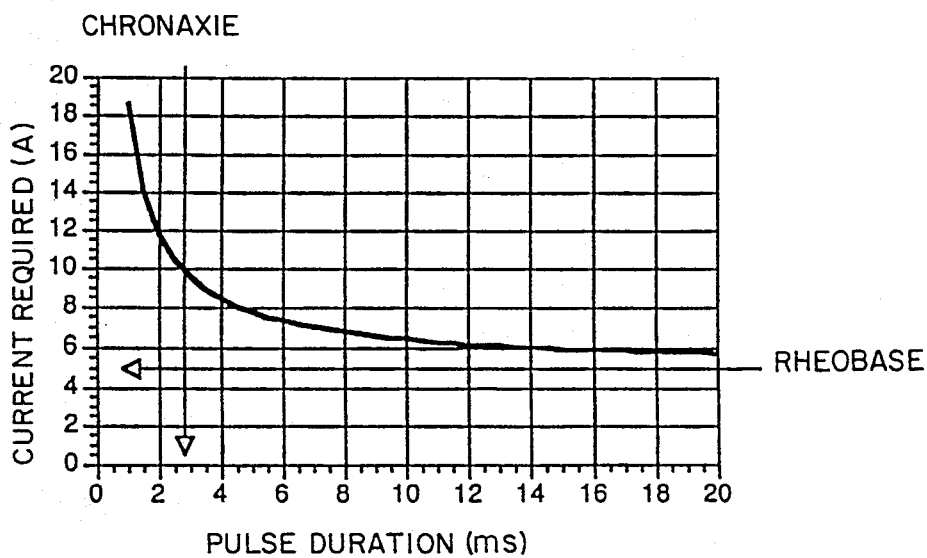
FIG. 3 illustrates a pulse being denominated by an absolute pulse width.

FIG. 3 illustrates a pulse being denominated by an absolute pulse width. The curve is a truncated decaying exponential defined by the pulse width and is 4.5 msec wide, and is expressed by equation 2 on page 7. By using a smaller value capacitor, there is a large percentage of energy delivered over a narrower pulse width.

Figure 4:
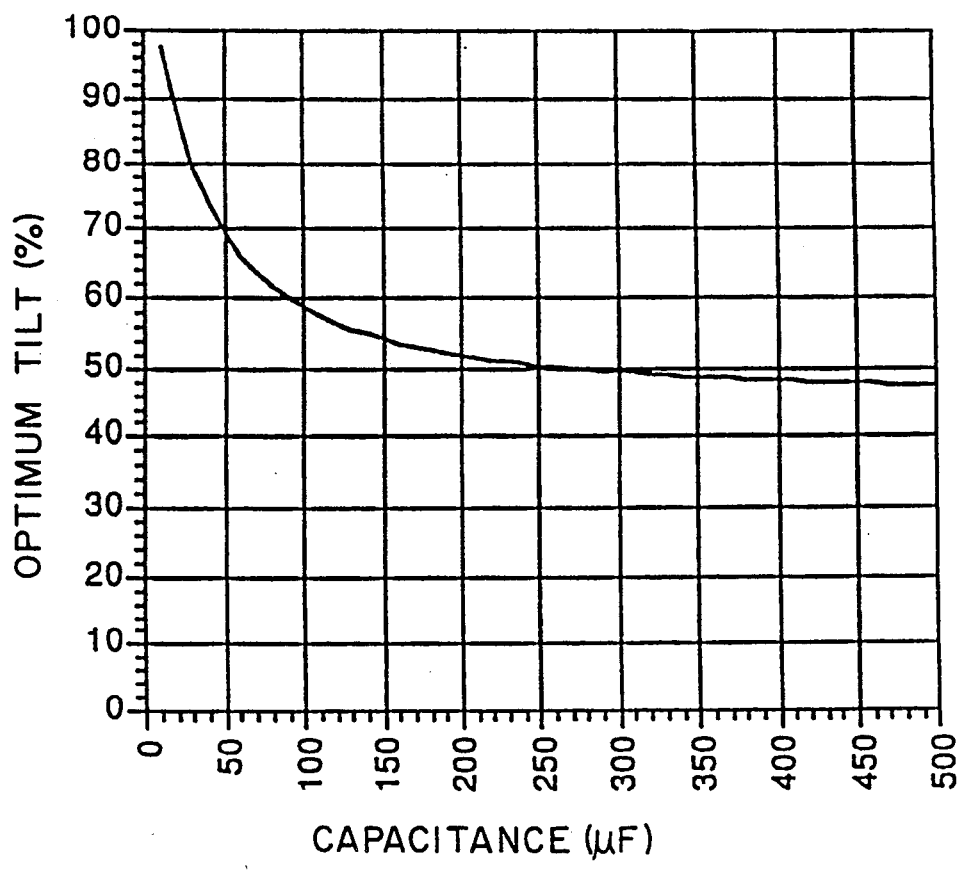
FIG. 4 illustrates a truncated capacitive discharge pulse.

FIG. 4 illustrates a truncated capacitive discharge pulse, denominated by tilt with cutoff at 66% tilt.

For physiologically effective current, the pulse width is expressed by the maximum P.E.C., the pulse width is given by:

$$d_p = \frac{RC + d_c}{e - 1} \quad \text{Eq. 5}$$

where $d_p$ = duration of the pulse
$d_c$ = chronaxie time
c = capacitance
R = total electrode-heart impedance
Thus for the optimum $d_p$:

$$\text{tilt} = 1 - e^{-d_p/RC} = 1 - \exp - \frac{1 + d_c/RC}{e - 1} \quad \text{Eq. 6}$$

The optimum capacitance value is independent of the stored energy.

The numerical solution to maximize PEC is: $RC = 0.8 d_c$
which is accurate to 1% over a broad range of the exogenous variables R and $d_c$.

This is a very reasonable result in that it implies that the RC time constant of the pulse should be close to the "time constant" (actually chronaxie time) of the myocardial cells for optimum performance.

One preferred embodiment uses a capacitor value of 43 uF and tilt of 72%. With initial voltage of 1195 V, this yields a stored energy of 30.7 J, and a physiologically effective current of $I_{pe}$ = 6.79 A.

Another preferred embodiment uses a capacitor value of 85 uF and a tilt of 61%. With initial voltage of 878 V, this yields a stored energy of 32.8 J, and a physiologically effective current of $I_{pe}$ = 6.79 A.

Still another preferred embodiment uses two capacitors in series, each of 178 uF, to provide 85 uF chargeable to 750 V. This yields a stored energy of 24 J and a physiologically effective current of $I_{pe}$ = 5.8 A.

The capacitance is chosen for the chronaxie time of the human heart, especially the heart strength duration curve. One range of preferred tilt is 50–63%.

MODE OF OPERATION

The present invention uses the chronaxie, a characteristic time that enters into heart defibrillation, that is defined by applying the model of L. Lapicque to defibrillation in accordance with the teachings of the present invention. In accordance with the teachings of the present invention, a figure of merit is defined as the physiologically effective current for characterizing and evaluating a defibrillation pulse. This figure of merit then further provides a comparison of defibrillation-pulse options and determines optima for capacitance, tilt and pulse duration as illustrated in the figures. The combined abilities of optima determination and quantitative comparison of options then leads to invoke shorter pulses and lower capacitance values than have been in use in the prior art. The overall result of this is the specifying of smaller, more efficient implantable defibrillator capacitor design than has been possible heretofore.

Various modifications can be made to the present invention without departing from the apparent scope hereof. The capacitors can be combined in parallel and/or series to achieve the desired capacitance. The defibrillation can be through an SVC electrode, a subcutaneous electrode, an RVA electrode or an optional housing electrode.

We claim:

1. An improved implantable defibrillator system for producing a capacitor-discharge defibrillation pulse, the implantable defibrillator system being a self-contained human implantable device including a pulse-generating capacitor means for storing an electrical charge, means for internally charging the pulse-generating capacitor means, and means for selectively discharging the electrical charge in the pulse-generating capacitor through electrodes implanted in a human patient in response to a sensing of a myocardial fibrillation in the human patient, the improvement comprising:

the pulse-generating capacitor means having an effective capacitance value in the range of 20–100 microfarads.

2. The system of claim 1 wherein the electrical charge stored in the capacitor means has an electrical energy of less than 30 joules.

3. The system of claim 1 wherein the capacitor means is charged initially to less than 1000 volts.

4. The system of claim 1 wherein the defibrillation pulse has a duration that is smaller than 5 milliseconds.

5. The system of claim 1 wherein an optimal capacitance value in the range of 20–100 microfarads is employed and determined so as to maximize a physiologically effective current for a given maximum electrical energy rating of a capacitor means.

6. The system of claim 1 wherein the electrical energy of the electrical charge stored to deliver a defibrillation pulse of a given effectiveness is minimized and determined by means of a physiologically effective current.

7. The system of claim 1 wherein the pulse-discharge capacitor is comprised of at least one electrolytic capacitor.

8. The system of claim 1 wherein a tilt value of the defibrillation pulse is between 50% and 63%.

* * * * *